(12) United States Patent
Nakajima et al.

(10) Patent No.: US 11,984,209 B2
(45) Date of Patent: May 14, 2024

(54) DRUG MANAGEMENT DEVICE, DRUG MANAGEMENT METHOD, AND NON-TRANSITORY RECORDING MEDIUM STORING PROGRAM FOR DRUG MANAGEMENT

(71) Applicant: OMRON HEALTHCARE Co., Ltd., Kyoto (JP)

(72) Inventors: Hiroshi Nakajima, Kyoto (JP); Daisuke Nozaki, Kyoto (JP); Fumihiko Nakamura, Kyoto (JP); Tamio Ueda, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 706 days.

(21) Appl. No.: 17/110,620

(22) Filed: Dec. 3, 2020

(65) Prior Publication Data
US 2021/0090701 A1 Mar. 25, 2021

Related U.S. Application Data

(63) Continuation of application No. PCT/JP2019/020320, filed on May 22, 2019.

(30) Foreign Application Priority Data

Jun. 8, 2018 (JP) .................................. 2018-110157

(51) Int. Cl.
*G16H 20/10* (2018.01)
*G16H 10/00* (2018.01)
(Continued)

(52) U.S. Cl.
CPC ............. *G16H 20/10* (2018.01); *G16H 10/00* (2018.01); *G16H 40/63* (2018.01); *G16H 40/67* (2018.01)

(58) Field of Classification Search
CPC ............................ G16H 20/10; G16H 70/40
See application file for complete search history.

(56) References Cited

U.S. PATENT DOCUMENTS 11,151,517 B2 * 10/2021 Herrin ................. G06Q 10/109
11,612,352 B1 * 3/2023 Kohli ................... A61B 5/4839
600/301
(Continued)

FOREIGN PATENT DOCUMENTS

CN 102646157 A 8/2012
CN 104188806 A 12/2014
(Continued)

OTHER PUBLICATIONS

International Preliminary Report on Patentability dated Dec. 10, 2020, in PCT/JP2019/020320.
(Continued)

*Primary Examiner* — Vincent H Tran
(74) *Attorney, Agent, or Firm* — Birch, Stewart, Kolasch & Birch, LLP

(57) ABSTRACT

A drug management device includes a first acquisition unit configured to acquire prescription data including data indicative of a drug prescribed to a subject, a second acquisition unit configured to acquire biometric data including data indicative of variations in a physical quantity of a living body of the subject, a first estimation unit configured to estimate, on the basis of the data indicative of variations in the physical quantity, whether or not the subject has taken the drug, and a second estimation unit configured to, in response to an estimation result indicating that the subject has taken the drug, estimate, on the basis of the data indicative of variations in the physical quantity, whether or not an effect of the drug on the subject satisfies an effect estimation criterion, which is predetermined.

7 Claims, 6 Drawing Sheets

(51) Int. Cl.
G16H 40/63 (2018.01)
G16H 40/67 (2018.01)

(56) References Cited

U.S. PATENT DOCUMENTS

| | | | |
|---|---|---|---|
| 2012/0143070 A1* | 6/2012 | Yao | G16H 10/60 |
| | | | 600/490 |
| 2012/0157793 A1 | 6/2012 | MacDonald | |
| 2013/0238119 A1* | 9/2013 | Simmons | A61J 7/0481 |
| | | | 700/237 |
| 2015/0157206 A1 | 6/2015 | Nakayama et al. | |
| 2016/0267309 A1* | 9/2016 | High | G16H 10/60 |
| 2016/0345877 A1* | 12/2016 | Takeuchi | A61B 5/7475 |
| 2018/0365385 A1* | 12/2018 | Cooney | G16H 20/60 |
| 2019/0200922 A1* | 7/2019 | Zhang | A61B 5/6843 |
| 2020/0027540 A1* | 1/2020 | Trübel | A61B 5/746 |
| 2020/0303050 A1* | 9/2020 | Sato | G16H 20/10 |
| 2020/0315512 A1* | 10/2020 | Komine | A61B 5/18 |

FOREIGN PATENT DOCUMENTS

| | | |
|---|---|---|
| JP | 2002-345759 A | 12/2002 |
| JP | 2012-130688 A | 7/2012 |
| JP | 2015-112205 A | 6/2015 |
| JP | 2015-228080 A | 12/2015 |
| JP | 2017-102614 A | 6/2017 |
| JP | 2017-176541 A | 10/2017 |
| JP | 2017-220012 A | 12/2017 |

OTHER PUBLICATIONS

Chinese Office Action and Search Report for Chinese Application No. 201980031673.4, dated Nov. 3, 2023, with English translation.

* cited by examiner

[FIG. 1]
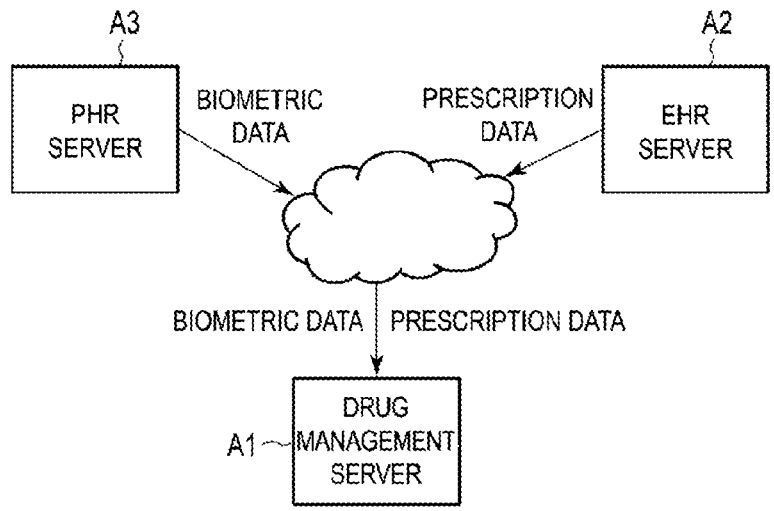
[FIG. 2]
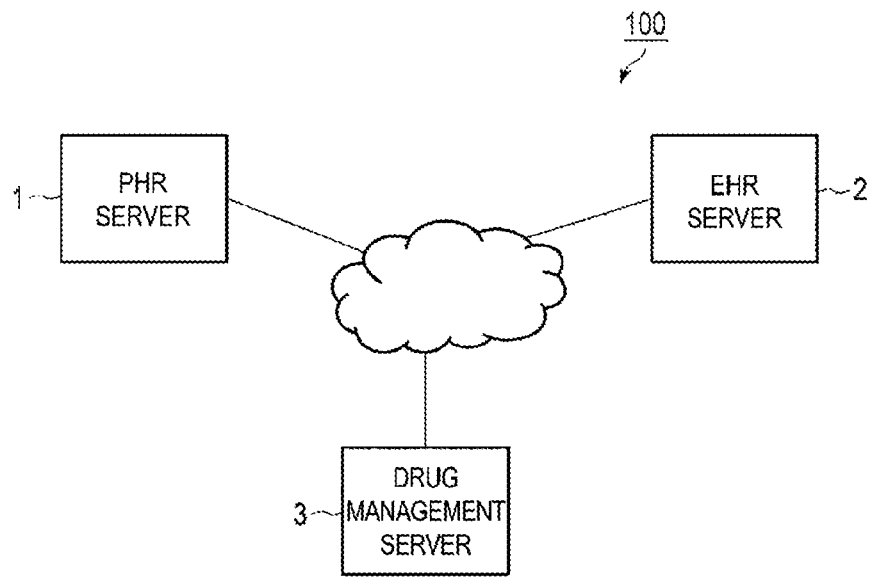

[FIG. 3]
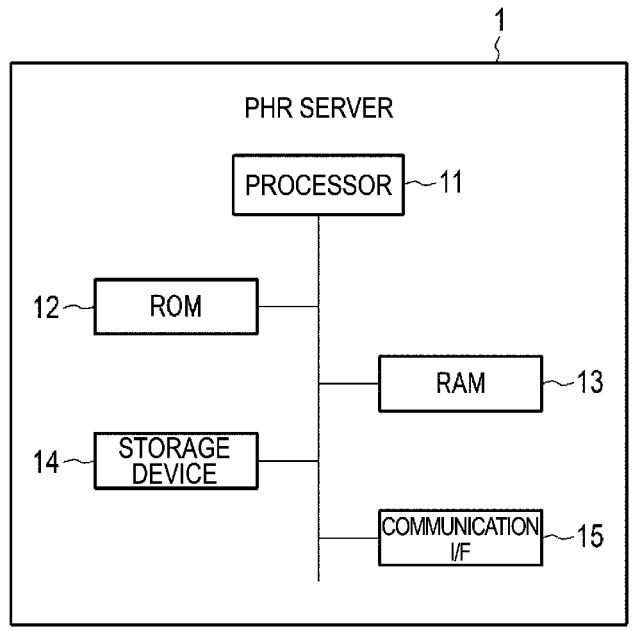
[FIG. 4]
| USER NAME | USER ID | ATTRIBUTE | | | PHYSICAL QUANTITY OF LIVING BODY | | |
|---|---|---|---|---|---|---|---|
| | | GENDER | AGE | NATIONALITY | BLOOD PRESSURE | BLOOD SUGAR LEVEL | HEART RATE |
| XXX | xxx | MALE | 35 | Japan | Yes | Yes | Yes |
| YYY | yyy | MALE | 60 | Japan | Yes | Yes | No |
| ZZZ | zzz | FEMALE | 30 | USA | Yes | No | No |
| ... | ... | ... | ... | ... | ... | ... | ... |

[FIG. 5]
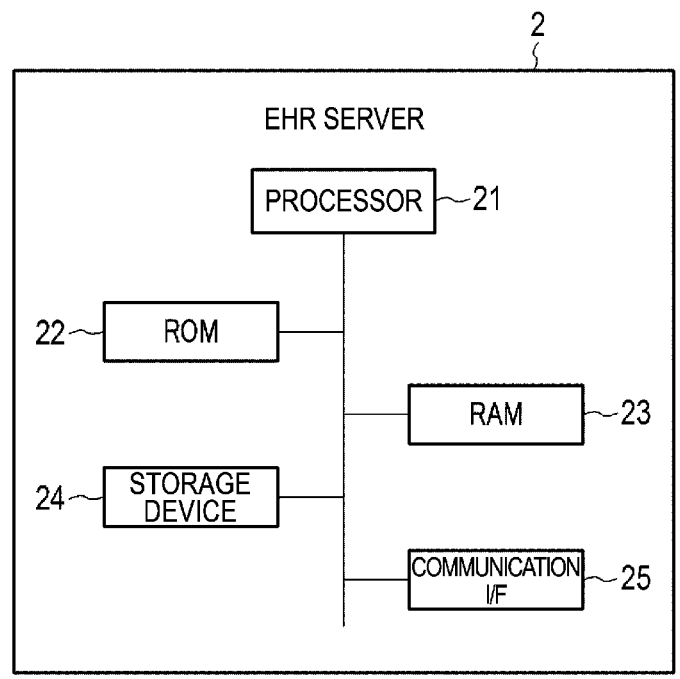

[FIG. 6]

| USER NAME | USER ID | ATTRIBUTE | | | | PRESCRIPTION DRUG | | | | | | | |
|---|---|---|---|---|---|---|---|---|---|---|---|---|---|
| | | GENDER | AGE | NATIONALITY | PRESCRIPTION DATE | SYMPTOMS | DRUG NAME | DRUG ID | PRESCRIPTION AMOUNT | TIMING OF TAKING DRUGS | AMOUNT TO TAKE DRUGS | EFFECT DURATION |
| XXX | xxx | MALE | 35 | Japan | 2018/01/13 | Hypertension | AAA | aaa | 20 | MORNING, EVENING | 1 | After 1 hour |
| YYY | yyy | MALE | 60 | Japan | 2018/02/20 | Hyperglycemia | BBB | bbb | 200 ml | EVENING | 10 ml | After 5 hours |
| ZZZ | zzz | FEMALE | 30 | USA | 2018/03/25 | Hypertension | CCC | ccc | 40 | MORNING, EVENING | 2 | After 4 hours |
| ... | ... | ... | ... | ... | ... | ... | ... | ... | ... | ... | ... | ... |

[FIG. 7]
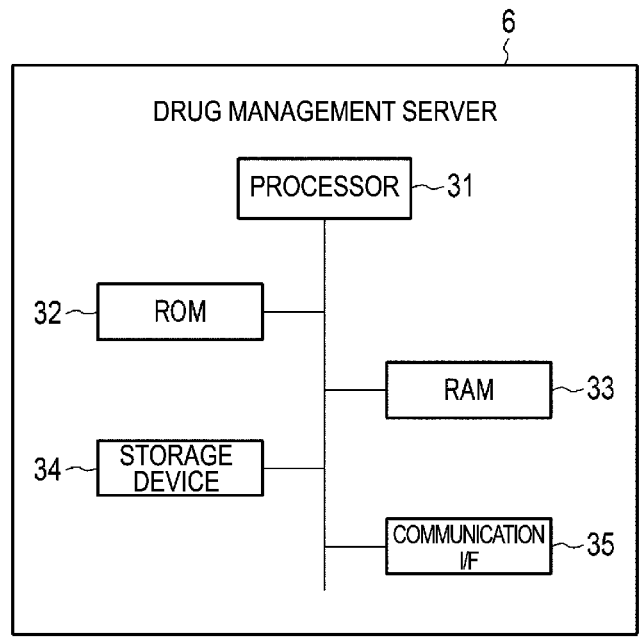
[FIG. 8]
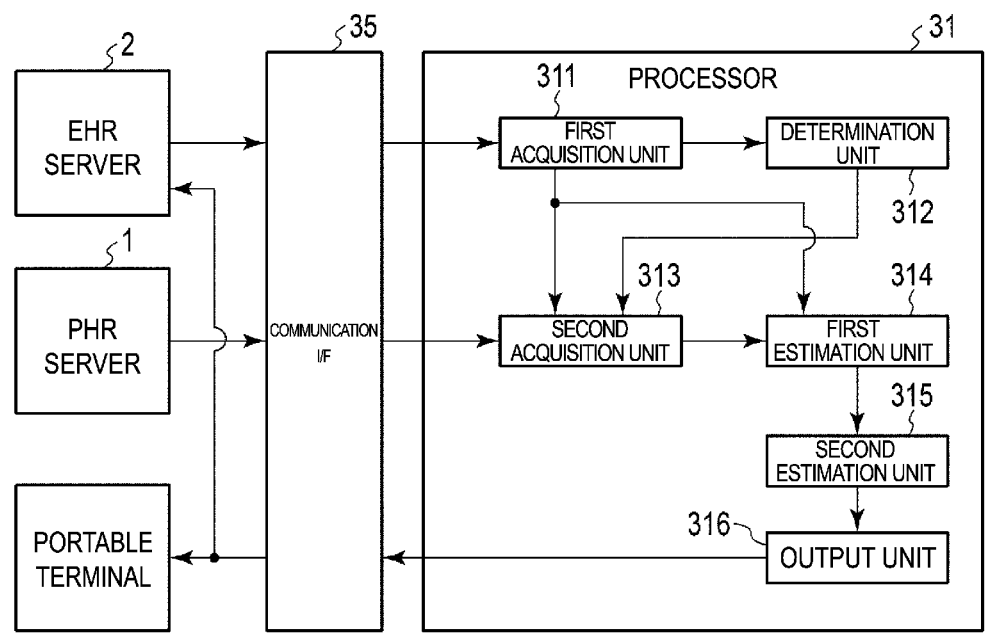

[FIG. 9]
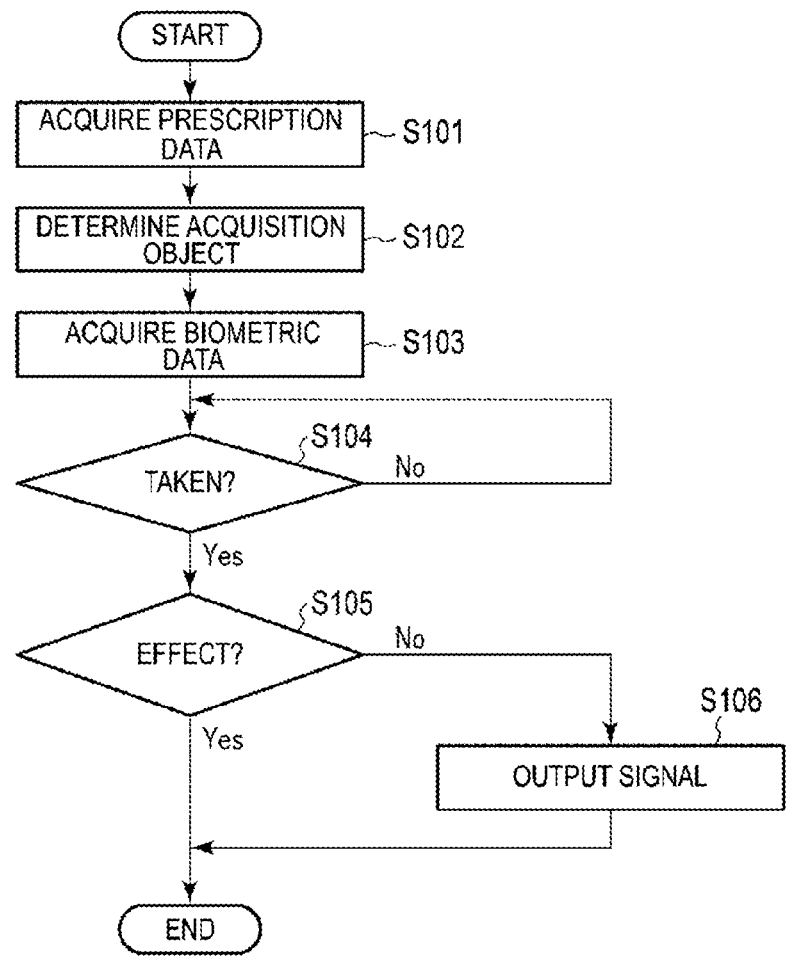

DRUG MANAGEMENT DEVICE, DRUG MANAGEMENT METHOD, AND NON-TRANSITORY RECORDING MEDIUM STORING PROGRAM FOR DRUG MANAGEMENT

This application is the U.S. national stage application filed pursuant to 35 U.S.C. 365(c) and 120 as a continuation of International Patent Application No. PCT/JP2019/020320, filed May 22, 2019, which application claims priority from Japanese Patent Application No. 2018-110157, filed Jun. 8, 2018, which applications are incorporated herein by reference in their entireties.

TECHNICAL FIELD

The invention relates to a drug management device, a drug management method, and a non-transitory recording medium storing a program for drug management that manage the effects of a drug on a subject.

BACKGROUND ART

As described in Patent Document 1, the development of technology for analyzing the effects of antihypertensive agents on blood pressure of subjects has been advancing.

The technology described in Patent Document 1 is a technology in which the dose period of the antihypertensive agent is read from a two-dimensional code and the effect of the antihypertensive agent is analyzed with blood pressure values during the dose period.

CITATION LIST

Patent Literature

Patent Document 1: JP 2017-176541

SUMMARY OF INVENTION

Technical Problem

However, in the technology described in Patent Document 1, it is assumed that the subject takes the antihypertensive agent during the dose period. If the subject fails to take the antihypertensive agent during the dose period, an incorrect analysis result such as the antihypertensive agent having no effect may be obtained. Thus, the technology described in Patent Document 1 has a problem in terms of analysis accuracy of the effects of the antihypertensive agent.

In light of the circumstances described above, an object of the present invention is to provide technology for improving the estimated accuracy of the effects of a drug on a subject.

Solution to Problem

A first aspect of the present disclosure is a drug management device including a first acquisition unit configured to acquire prescription data including data indicative of a drug prescribed to a subject, a second acquisition unit configured to acquire biometric data including data indicative of variations in a physical quantity of a living body of the subject, a first estimation unit configured to estimate, on the basis of the data indicative of variations in the physical quantity, whether or not the subject has taken the drug, and a second estimation unit configured to, in response to an estimation result indicating that the subject has taken the drug, estimate, on the basis of the data indicative of variations in the physical quantity, whether or not an effect of the drug on the subject satisfies an effect estimation criterion, which is predetermined.

According to the first aspect, the drug management device can improve the estimation accuracy of the effect of the drug on the subject by assuming an estimated operation of taking the drug as a premise of an estimated operation of effect of the drug.

A second aspect of the present disclosure is the first aspect, further including a determination unit configured to determine a type of the physical quantity to be acquired, on the basis of the data indicative of the drug.

The physical quantity that varies is different depending on the drug. According to the second aspect, the drug management device can determine, on the basis of the drug, the type of physical quantity suitable for estimating whether or not the subject has taken the drug and for estimating the effect of the drug on the subject.

A third aspect of the present disclosure is the first aspect, further including an output unit configured to output a signal for supporting the subject in response to an estimation result indicating that an effect of the drug on the subject does not satisfy the effect estimation criterion.

According to a third aspect, the drug management device can notify a subject that the effect of the drug does not satisfy the effect estimation criterion, and may prompt the subject to reserve a consultation or prescription of the drug at a hospital. The drug management device can use the effect estimation criterion for each person to perform support on each person without variation.

A fourth aspect of the present disclosure is the first aspect, wherein the prescription data includes data indicative of timing of taking drugs and data indicative of effect duration after taking the drug, and the first estimation unit specifies, on the basis of the timing of taking drugs and the effect duration, a time period for estimating whether or not the drug has been taken, and estimates, on the basis of data relating to the time period among the data indicative of variations in the physical quantity, whether or not the drug has been taken.

Even in a situation where the subject is not taking the drug, the value based on the estimation target data may temporarily be equal to or greater than the first threshold. According to the fourth aspect, by estimating, on the basis of the data relating the specified time period, whether or not the subject has taken the drug, the drug management device can improve the estimation accuracy of whether or not the subject has taken the drug. As a result, the drug management device can improve the estimation accuracy of whether or not the effect of the drug on the subject satisfies the effect estimation criterion. Furthermore, the drug management device can reduce the load of the estimation operation by omitting the estimation operation in time periods other than the specified time period.

A fifth aspect of the present disclosure is the first aspect, wherein the prescription data includes data indicative of a symptom of the subject, the effect estimation criterion includes a criterion for each symptom, and the second estimation unit estimates, with using a criterion corresponding to a symptom of the subject, whether or not an effect of the drug on the subject satisfies the effect estimation criterion.

The amount of variation of the physical quantity due to taking the drug is different depending on the symptom. According to the fifth aspect, the drug management device can improve the estimation accuracy of the effect of the drug on the subject by using the criterion corresponding to the symptom of the subject.

A sixth aspect of the present disclosure is the first aspect, wherein the effect estimation criterion includes a criterion for each drug, and the second estimation unit estimates, with using a criterion corresponding to the drug prescribed to the subject, whether or not an effect of the drug on the subject satisfies the effect estimation criterion.

Even with the same symptom, the amount of variation of the physical quantity is different depending on the drug taken by the subject. According to the sixth aspect, the drug management device can improve the estimation accuracy of the effect of the drug on the subject by using the criterion corresponding to the drug prescribed to the subject.

A seventh aspect of the present disclosure is the first aspect, wherein the prescription data or the biometric data includes data indicative of an attribute of the subject, the effect estimation criterion includes a criterion for each attribute, and the second estimation unit estimates, with using a criterion corresponding to an attribute of the subject, whether or not an effect of the drug on the subject satisfies the effect estimation criterion.

In a case in which people with different attributes take the same drug, the amount of variation of the physical quantity is different. According to the seventh aspect, the drug management device can improve the estimation accuracy of the effect of the drug on the subject by using the criterion corresponding to the attribute of the subject.

An eighth aspect of the present disclosure is a drug management method, including, a first acquisition step of acquiring prescription data including data indicative of a drug prescribed to a subject, a second acquisition step of acquiring biometric data including data indicative of variations in a physical quantity of a living body of the subject, a first estimation step of estimating, on the basis of the data indicative of variations in the physical quantity, whether or not the subject has taken the drug, and a second estimation step of, in response to an estimation result indicating that the subject has taken the drug, estimating, on the basis of the data indicative of variations in the physical quantity, whether or not an effect of the drug on the subject satisfies an effect estimation criterion, which is predetermined.

According to the eighth aspect, the drug management method can obtain the same effects as the first aspect described above.

A ninth aspect of the present disclosure is a non-transitory recording medium storing a program for drug management that causes a computer to perform processing of each unit provided in the drug management device according to any one of the first to seventh aspects.

According to the ninth aspect, the non-transitory recording medium storing a program for drug management can obtain the same effects as the first aspect described above.

Advantageous Effects of Invention

According to the present invention, technology to improve the estimation accuracy of the effects of a drug on a subject can be provided.

BRIEF DESCRIPTION OF DRAWINGS

FIG. 1 is a diagram schematically illustrating an application example of a drug management server according to the present embodiment.

FIG. 2 is a diagram illustrating an example of the overall configuration of a drug management system according to the present embodiment.

FIG. 3 is a block diagram illustrating an example of the hardware configuration of a PHR server according to the present embodiment.

FIG. 4 is a diagram illustrating an example of a PHR database stored in the PHR server according to the present embodiment.

FIG. 5 is a block diagram illustrating an example of the hardware configuration of an EHR server according to the present embodiment.

FIG. 6 is a diagram illustrating an example of an EHR database stored in the EHR server according to the present embodiment.

FIG. 7 is a block diagram illustrating an example of the hardware configuration of a drug management server according to the present embodiment.

FIG. 8 is a block diagram illustrating an example of the software configuration of the drug management server according to the present embodiment.

FIG. 9 is a flowchart illustrating an example of an effect estimation operation of the drug management server according to the present embodiment.

DESCRIPTION OF EMBODIMENTS

An embodiment according to the present invention (hereinafter, also referred to as "the present embodiment") will be described below with reference to the drawings. However, the present embodiment described below is merely an example in all respects. Note that elements that are the same as or similar to the elements described hereinafter are given the same or similar reference signs, and duplicate descriptions will be omitted.

1 Application Example

The present embodiment is technology for managing, on the basis of biometric data and prescription data for each person, the effects of a prescribed drug on persons.

FIG. 1 is a diagram schematically illustrating an application example of a drug management server A1.

The drug management server A1 acquires prescription data from an electronic health records (EHR) server A2. The prescription data is data relating to the drug prescribed to a subject. The prescription data includes data indicative of the drug prescribed to the subject. The drug management server A1 acquires biometric data from a personal health records (PHR) server A3. Biometric data is data that includes data indicative of variations in a physical quantity of a living body of the subject.

The drug management server A1 estimates, on the basis of the data indicative of variations in the physical quantity, whether or not the subject has taken the drug. The drug management server A1 estimates, on the basis of the data indicative of the variations in the physical quantity, whether or not the effects of the drug on the subject satisfy a predetermined effect estimation criterion, in response to the estimation result indicating that the subject used the drug. The effect estimation criterion is a standard for estimating whether or not a drug had a predetermined effect on a subject. The drug management server A1 can perform support on the subject in response to an estimation result indicating that the effect of the drug on the subject does not satisfy the effect estimation criterion. For example, the drug management server A1 can perform support on the subject by informing the subject that the effect of the drug does not satisfy the effect estimation criterion. For example, the drug management server A1 can perform support on the subject by encouraging the subject to reserve a consultation or prescription of a different drug at a hospital.

In this manner, the drug management server A1 can use in conjunction the prescription data of each person stored in the EHR server A2 and the biometric data of each person stored in the PHR server A3. The drug management server A1 can provide technology to improve the estimation accuracy of the effects of the drug on the subject.

2 Configuration Example

Drug Management System

FIG. 2 illustrates an example of the overall configuration of a drug management system 100.

The drug management system 100 includes a personal health records (PHR) server 1, an electronic health records (EHR) server 2, and a drug management server 3. The PHR server 1, the EHR server 2, and the drug management server 3 can communicate with each other over a network. The network, for example, is the Internet.

The PHR server 1 is a server that collects and manages data indicative of variations in a physical quantity of the living body of persons. Data indicative of variations in a physical quantity of the living body is also referred to as physical quantity data. The physical quantity data is data including a physical quantity of the living body associated with the measurement time of the physical quantity of the living body. The physical quantity of the living body is the physical quantity measured from the living body. For example, the physical quantity of the living body is, but is not limited to, blood pressure, blood sugar level, heart rate, and electrocardiogram. The physical quantity of the living body is measured by a measurement instrument capable of continuous measurement. For example, blood pressure is measured by a blood pressure monitor capable of continuously measuring each heartbeat. Alternatively, or in conjunction therewith, the physical quantity of the living body may be measured by a measurement instrument that measures on the basis of each person's measurement instruction. For example, blood pressure may be measured by a blood pressure monitor that measures on the basis of each person's measurement instruction. The method of measuring a physical quantity of the living body may be, but it not limited to, a method using a pressure sensor or a method using a photoelectric sensor. The PHR server 1 may obtain the physical quantity data directly from the measurement instrument or via a portable terminal such as a smartphone.

The EHR server 2 is a server that manages data relating to the drug prescribed to each person. For example, the EHR server 2, in conjunction with an electronic medical chart that is input by a doctor using a personal computer (PC), collects data relating to the drug prescribed to each person. Alternatively or in addition to, the EHR server 2, in conjunction with the data that is input by a pharmacist using a PC, may collect data relating to the drug prescribed to each person.

The drug management server 3 is a server that uses in conjunction the physical quantity data of each person stored in the PHR server 1 and the data relating to the drug prescribed to each person stored in the EHR server 2. The drug management server 3 manages the effects of the prescribed drug on each person, on the basis of the physical quantity data of each person and the data relating to the drug prescribed to each person. The residual amount of the drug is also referred to as the residual drug amount. The drug management server 3 is also referred to as a drug management device.

PHR Server

Hardware Configuration

FIG. 3 is a block diagram illustrating an example of the hardware configuration of the PHR server 1.

The PHR server 1 includes a processor 11, a read only memory (ROM) 12, a random access memory (RAM) 13, a storage device 14, and a communication interface 15. Each element is electrically connected to one another. Note that, in FIG. 3, the communication interface is indicated as "communication I/F".

The processor 11 controls each element of the PHR server 1. For example, the processor 11 is a central processing unit (CPU), but is not limited thereto. The processor 11 deploys a program to RAM 13, the program is for executing the PHR server 1 and is stored in the storage device 14. The processor 11 subsequently interprets and executes the program deployed in the RAM 13, and thus the processor 11 can execute various operations.

The storage device 14 is a so-called auxiliary storage device. For example, the storage device 14 is a hard disk drive (HDD), but is not limited thereto. The storage device 14 stores the program to be executed by the processor 11. Note that the program may be stored in the storage device 14 in advance. The program may be downloaded to the PHR server 1 via a network. The program may be stored and distributed on a non-transitory computer-readable medium.

The storage device 14 stores a PHR database. The PHR database is a database that manages the physical quantity data of each person. Examples of configurations of the PHR database are described below.

The communication interface 15 is an interface for the PHR server 1 to communicatively connect to other devices. The communication interface 15 may include an interface for wired communication or an interface for wireless communication.

Note that, with regard to a specific hardware configuration of the PHR server 1, components can be omitted, replaced, and added as appropriate according to the embodiment. For example, the PHR server 1 may include a plurality of processors.

PHR Database Configuration

FIG. 4 is a diagram illustrating an example of a PHR database stored in the storage device 14 of the PHR server 1. The PHR database includes items of user name, user ID, attributes, and physical quantity of the living body. The user name item is an item that indicates the name of each person. The user ID item is an item that indicates the identification information uniquely assigned to each person. The attributes item is an item that indicates the features of each person. The attributes item includes items of gender, age, and nationality. The physical quantity of the living body item is an item that indicates the presence or absence of physical quantity data measured from each person's living body. The physical quantity of the living body item includes items of blood pressure, blood sugar level, and heart rate. For example, in the case in which the blood pressure item indicates "YES", the storage device 14 is storing data indicative of variations in the person's blood pressure. On the other hand, in the case in which the blood pressure item indicates "NO", the storage device 14 is not storing data indicative of variations in the person's blood pressure. The same applies to the items of blood sugar level and heart rate.

Note that the PHR database may include items other than the items of user name, user ID, attributes, and physical quantity of the living body. The PHR database may not include the item of user name or the user ID. The PHR database may not include the attributes item. Note that attributes item may include other items in addition to the items of gender, age, and nationality. The attributes item may include other items instead of at least one of the items of gender, age, or nationality. The attributes item may not include at least one of the items of gender, age, and nationality. The physical quantity of the living body item may include items of other types of physical quantities in addition to the items of blood pressure, blood sugar level, and heart rate. The physical quantity of the living body item may include items of other types of physical quantities instead of at least one of the items of blood pressure, blood sugar level, and heart rate.

The processor 11 manages data corresponding to each item in the PHR database, as described below. Data indicative of the user name, data indicative of the user ID, and data indicative of the attributes are registered in advance by each person. The data indicative of the user name is also referred to as user name data. The data indicative of the user ID is also referred to as user ID data. The data indicative of the attributes is also referred to as attributes data.

The physical quantity data is managed as described below. The processor 11 references the user ID added to the physical quantity data, each time the physical quantity data is acquired from the measurement instrument or the portable terminal via the communication interface 15. The processor 11 determines whether the currently acquired physical quantity of the living body is a previously acquired type of physical quantity. In the case in which the currently acquired physical quantity of the living body is a physical quantity of a previously unacquired type, the processor 11 sets the item of the currently acquired physical quantity of the living body to "YES". The processor 11 stores the currently acquired physical quantity data in the storage device 14. In the case in which the currently acquired physical quantity of the living body is a physical quantity of a previously acquired type, the processor 11 stores the currently acquired physical quantity data in the storage device 14. The processor 11 associates the currently acquired physical quantity data with the same type of physical quantity data that is previously received and stored in the storage device 14.

The processor 11 references the PHR database and transmits the biometric data of the subject to the drug management server 3, as described below. First, the processor 11 receives a PHR request from the drug management server 3. The PHR request is a request for biometric data, which includes physical quantity data of the subject, from the drug management server 3 to the PHR server 1. The PHR request includes data specifying the biometric data to be acquired. For example, the PHR request includes at least user ID data, data indicative of a type of physical quantity to be acquired, and data specifying the time period of physical quantity data. The data specifying the time period includes at least a start date and time of the time period. The data specifying the time period may include a time period before the date and time when the drug management server 3 sends the PHR request to the PHR server 1 (hereinafter, also referred to as the PHR request transmission date and time). The data specifying the time period may be data specifying a time period from the start date and time, which is before the PHR request transmission date and time, to the end date and time, which is before the PHR request transmission date and time. The data specifying the time period may be data specifying a time period from the start date and time, which is before the PHR request transmission date and time, to an end date and time, which is after the PHR request transmission date and time. The data specifying the time period may be data specifying a time period from the start date and time, which is after the PHR request transmission date and time, to the end date and time, which is after the PHR request transmission date and time. The data specifying the time period may be data specifying a start date and time, which is before the PHR request transmission date and time, and not specifying an end date and time, which is after the PHR request transmission date and time. The data specifying the time period may be data specifying a start date and time, which is after the PHR request transmission date and time, and not specifying an end date and time, which is after the PHR request transmission date and time.

The processor 11 then references the data in the PHR database that is associated with the user ID included in the PHR request. Next, the processor 11 references the physical quantity of the living body item in the PHR database to determine the presence or absence of a physical quantity to be acquired. In the case in which there is no physical quantity to be acquired, the processor 11 transmits a response to the drug management server 3 indicating that there is no physical quantity to be acquired.

On the other hand, in the case in which there is a physical quantity to be acquired, the processor 11 acquires the physical quantity data to be acquired from the storage device 14. In the case in which the data specifying the time period includes a time period before the PHR request transmission date and time, the processor 11 generates biometric data including the physical quantity data for the time period before the PHR request transmission date and time. The biometric data includes data of at least one of: the user name data or the user ID data. The biometric data may include attributes data. The processor 11 transmits the biometric data to the drug management server 3.

In the case in which the data specifying the time period includes specifying after the PHR request transmission date and time, the processor 11 generates, after the PHR request transmission date and time, biometric data including the physical quantity data. The biometric data includes data of at least one of: the user name data or the user ID data. The biometric data may include attributes data. As described below, the processor 11 transmits, after the PHR request transmission date and time, to the drug management server 3, the biometric data including the physical quantity data after the PHR request transmission date and time. In one example, the processor 11 can continuously transmit, to the drug management server 3, the biometric data including the physical quantity data after the PHR request transmission date and time. In another example, the processor 11 can transmit, to the drug management server 3, the biometric data including the physical quantity data of a certain time period, each time the certain time period elapses after the PHR request transmission date and time. The period of time may be an amount of time or days.

EHR Server

Hardware Configuration

FIG. 5 is a block diagram illustrating an example of the hardware configuration of the EHR server 2.

The EHR server 2 includes a processor 21, a ROM 22, a RAM 23, a storage device 24, and a communication interface 25. Each element is electrically connected to one another. Note that, in FIG. 5, the communication interface is indicated as "communication I/F".

The processor 21 controls each element of the EHR server 2. For example, the processor 21 is a CPU, but is not limited thereto. The processor 21 deploys a program to RAM 23, the program is for executing the EHR server 2 and is stored in the storage device 24. The processor 21 subsequently interprets and executes the program deployed in the RAM 23, and thus the processor 21 can execute various operations.

The storage device 24 is a so-called auxiliary storage device. For example, the storage device 24 is an HDD, but is not limited thereto. The storage device 24 stores the program to be executed by the processor 21. Note that the program may be stored in the storage device 24 in advance. The program may be downloaded to the EHR server 2 via a network. The program may be stored and distributed on a non-transitory computer-readable medium.

The storage device 14 stores an EHR database. The EHR database is a database that manages data relating to the drug prescribed to each person. Examples of configurations of the EHR database are described below.

The communication interface 25 is an interface for the EHR server 2 to communicatively connect to other devices. The communication interface 25 may include an interface for wired communication or an interface for wireless communication.

Note that, with regard to a specific hardware configuration of the EHR server 2, components can be omitted, replaced, and added as appropriate according to the embodiment. For example, the EHR server 2 may include a plurality of processors.

EHR Database Configuration

FIG. 6 is a diagram illustrating an example of the EHR database stored in the storage device 24 of the EHR server 2. The EHR database manages data relating to the drug prescribed to each person. The EHR database includes items of user name, user ID, attributes, and prescription drug. As in the PHR database, the user name item is an item that indicates the name of each person. As in the PHR database, the user ID item is an item that indicates the identification information uniquely assigned to each person. As in the PHR database, the attributes item is an item that indicates the features of each person. The attributes item includes items of gender, age, and nationality.

The prescription drug data item is an item relating to the drug prescribed to each person. The prescription drug item includes items of prescription date, symptoms, drug name, drug ID, prescription amount, timing of taking drugs, amount to take drugs, and effect duration. The prescription date item is an item that indicates the date when the drug was prescribed to each person. The symptom item is an item that indicates the symptom of each person diagnosed by a doctor as the prescription reason for the drug. The drug name item is an item that indicates the name of the drug prescribed to each person. The drug ID item is an item that indicates the identification information uniquely assigned to the drug prescribed to each person. The prescription amount item is an item that indicates the prescribed amount of the drug for each person. The prescribed amount item indicates, but is not limited to, the number or liquid amount. The timing of taking drugs item is an item that indicates timing of taking the each person's drug. The timing of taking drugs item indicates at least one of morning, day, or night, but is not limited thereto. The amount to take drugs item is an item that indicates the amount of drug taken each time by each person. The amount to take drugs item indicate, but is not limited to, the number or liquid amount. The effect duration item is an item that indicates the approximate time the effect lasts after each person has taken the drug. Note that "drug" used in the present embodiment includes various types. For example, "drug" includes, but is not limited to, orally taken drugs, drugs for pasting, drugs for applying, drugs used for radiation, and self-injected drugs. The term "take" used in this embodiment includes various forms depending on the type of drug. For example, "take" includes, but is not limited to, orally taking, pasting, applying, radiation, and injection.

Note that the EHR database may include items other than the items of user name, user ID, attributes, and prescription drug. The EHR database may not include the item of user name or the user ID. The EHR database may not include the attributes item. The attributes item may include other items in addition to the items of gender, age, and nationality. The attributes item may include other items instead of at least one of the items of gender, age, or nationality. The attributes item may not include at least one of the items of gender, age, and nationality. The prescription drug items may include other items in addition to the items of prescription date, symptoms, drug name, drug ID, prescription amount, timing of taking drugs, amount to take drugs, and effect duration. The prescription drug items may include other items instead of at least one of the items of prescription date, symptoms, drug name, drug ID, prescription amount, timing of taking drugs, amount to take drugs, and effect duration.

The processor 21 manages data corresponding to each item in the EHR database, as described below. The processor 21 receives, via the communication interface 25, data of the electronic medical chart that is input by a doctor using the PC. The processor 21 extracts data corresponding to each item in the EHR database on the basis of the data of the electronic medical chart. The processor 21 manages the extracted data in the EHR database. Note that the processor 21 may extract data corresponding to each item in the EHR database on the basis of the data that is input by a pharmacist using the PC.

The processor 21 references the EHR database and transmits the prescription data, relating to the drug prescribed to the subject, to the drug management server 3 as described below. The prescription data relating to the drug prescribed to the subject is also referred to as prescription data of the subject. In one example, the processor 21 transmits the prescription data of the subject to the drug management server 3, on the basis of an EHR request from the drug management server 3. The EHR request is a request for the prescription data of the subject from the drug management server 3 to the EHR server 2. In this example, first, a processor 31 receives an EHR request from the drug management server 3 via a communication interface 35. Next, the processor 11 extracts, from the EHR database, prescription date within a predetermined time period including the receipt date and time of the EHR request. The processor 11 then extracts data relating to the subject associated with the extracted prescription date from the EHR database and generates the prescription data of the subject. The processor 11 then transmits the prescription data of the subject to the drug management server 3.

In another example, the processor 21 autonomously transmits the prescription data of the subject to the drug management server 3. In this example, first, the processor 21 determines, on the basis of the addition of the new prescription drug data in the EHR database, the subject related to the newly added prescription drug data. The processor 21 then extracts data relating to this subject from the EHR database and generates the prescription data of the subject. The processor 11 then transmits the prescription data of the subject to the drug management server 3.

The prescription data includes data indicative of the user name data, the user ID data, and the prescription drug. The data indicative of the prescription drug is also referred to as prescription drug data. The prescription drug data includes data indicative of the prescription date, data indicative of the symptoms, data indicative of the drug name, data indicative of the drug ID, data indicative of the prescription amount, data indicative of the timing of taking drugs, data indicative of the amount to take drugs, and data indicative of the effect duration. The data indicative of the prescription date is also referred to as prescription date data. The data indicative of the symptoms is also referred to as symptom data. The data indicative of the drug name is also referred to as drug name data. The data indicative of the drug ID is also referred to as drug ID data. The data indicative of the prescription amount is also referred to as prescription amount data. The data indicative of the timing of taking drugs is also referred to as timing of taking drugs data. The data indicative of the amount to take drugs is also referred to as amount to take drugs data. The data indicative of the effect duration is also referred to as effect duration data. The prescription date data is data indicative of the date when the drug was prescribed to the subject. The symptom data includes data indicative of the symptoms of the subject. The drug name data is data indicative of the name of the drug prescribed to the subject. Thus, the drug name data can also be considered as data indicative of the drug prescribed to the subject. The drug ID data is data indicative of the identification information uniquely assigned to the drug prescribed to the subject. Thus, the drug ID data can also be considered as data indicative of the drug prescribed to the subject. The prescription amount data is data indicative of the prescription amount of the drug for the subject. The timing of taking drugs data is data indicative of timing of taking the drug for the subject. The amount to take drugs data is data indicative of the amount of drug taken each time by the subject. The effect duration data is data indicative of the effect duration after the subject has taken the drug.

Note that the prescription data may include attributes data. The prescription data may not include one from among the user name data or the user ID data. The data indicative of the prescription drug may not include at least one from among the prescription date data, the symptom data, the drug name data, the drug ID data, the prescription amount data, the timing of taking drugs data, the amount to take drugs data, and the effect duration data. The data indicative of the prescription drug may include other data relating to the drug prescribed to the subject instead of one from among the prescription date data, the symptom data, the drug name data, the drug ID data, the prescription amount data, the timing of taking drugs data, the amount to take drugs data, and the effect duration data.

Drug Management Server

Hardware Configuration

FIG. 7 is a block diagram illustrating an example of the hardware configuration of the drug management server 3.

The drug management server 3 includes a processor 31, a ROM 32, a RAM 33, a storage device 34, and a communication interface 35. Each element is electrically connected to one another. Note that, in FIG. 7, the communication interface is indicated as "communication I/F".

The processor 31 controls each element of the drug management server 3. For example, the processor 31 is a CPU, but is not limited thereto. The processor 31 deploys a program to the RAM 33, the program is for executing the drug management server 3 and is stored in the storage device 34. The processor 31 subsequently interprets and executes the program deployed in the RAM 33, and thus the processor 31 can execute each unit described in the software configuration section.

The storage device 34 is a so-called auxiliary storage device. For example, the storage device 34 is an HDD, but is not limited thereto. The storage device 34 stores the program to be executed by the processor 31. The program is for executing the EHR server 2 as the units described in the software configuration section. Note that the program may be stored in the storage device 34 in advance. The program may be downloaded to the drug management server 3 via a network. The program may be stored and distributed on a non-transitory computer-readable medium.

The communication interface 35 is an interface for the drug management server 3 to communicatively connect to other devices. The communication interface 35 may include an interface for wired communication or an interface for wireless communication.

Note that, with regard to a specific hardware configuration of the drug management server 3, components can be omitted, replaced, and added as appropriate according to the embodiment. For example, the drug management server 3 may include a plurality of processors.

Software Configuration

FIG. 8 is a block diagram illustrating an example of the software configuration of the drug management server 3.

The processor 31 implements a first acquisition unit 311, a determination unit 312, a second acquisition unit 313, a first estimation unit 314, a second estimation unit 315, and an output unit 316.

The first acquisition unit 311 will be described. As illustrated below, the first acquisition unit 311 acquires the prescription data relating to the drug prescribed to the subject. The prescription data includes the drug ID data or the drug name data. In one example, the first acquisition unit 311 obtains the prescription data of the subject as a response to an EHR request from the drug management server 3 to the EHR server 2 via the communication interface 35. In another example, the first acquisition unit 311 acquires the prescription data of the subject autonomously transmitted by the EHR server 2 via the communication interface 35. The first acquisition unit 311 outputs the prescription data to the determination unit 312, the second acquisition unit 313, and the first estimation unit 314.

The determination unit 312 will be described. The determination unit 312 determines, on the basis of the drug ID data or the drug name data, the type of physical quantity to be acquired, as described below. The determination unit 312 refers to a database in which the drug ID, which is stored in advance in the storage device 14, is associated with the physical quantity of the living body, which is assumed to vary due to the drug corresponding to the drug ID. The determination unit 312 references the database and determines a physical quantity of the living body, which is assumed to vary due to the drug identified from the drug ID data included in the prescription data. The physical quantity of the living body, which is assumed to vary, corresponds to the physical quantity to be acquired. In this way, the determination unit 312 determines the type of the physical quantity to be acquired. The determination unit 312 outputs a determination result indicative of the type of physical quantity to be acquired to the second acquisition unit 313. Note that the determination unit 312 may refer to the drug name data instead of the drug ID data and determine the type of physical quantity to be acquired by the same process as that described above.

The second acquisition unit 313 will be described. As described below, the second acquisition unit 313 acquires biometric data indicative of the physical quantity data of the subject. The second acquisition unit 313 acquires the prescription data from the first acquisition unit 311. The second acquisition unit 313 acquires the user ID data from the prescription data. The second acquisition unit 313 acquires the determination result from the determination unit 312. The second acquisition unit 313 acquires data indicative of the type of physical quantity to be acquired from the determination result. The second acquisition unit 313 discretionarily sets data specifying the time period of the physical quantity data. The second acquisition unit 313 generates a PHR request. The PHR request includes at least the user ID data of the subject, data indicative of the type of the physical quantity to be acquired, and data specifying the time period of the physical quantity data. The second acquisition unit 313 transmits the PHR request to the PHR server 1. The second acquisition unit 313 acquires, via the communication interface 35, biometric data including the physical quantity data of the subject from the PHR server 1, as a response to the PHR request. The second acquisition unit 313 outputs the biometric data of the subject to the first estimation unit 314.

The first estimation unit 314 will be described. The first estimation unit 314 estimates, on the basis of the physical quantity data, whether or not the subject has taken the drug, as described below. Here, the physical quantity data used to estimate whether or not the subject has taken the drug is referred as to estimation target data. For example, the first estimation unit 314 uses a criterion for estimation of taking to estimate whether or not the subject has taken the drug. The criterion for estimation of taking is a criterion for estimating whether or not the subject has taken the drug. The criterion for estimation of taking is predetermined. Some examples of the criterion for estimation of taking are described below. The first estimation unit 314 compares the estimation target data to the criterion for estimation of taking. The first estimation unit 314 estimates, depending on whether or not the estimation target data satisfies the criterion for estimation of taking, whether or not the subject has taken the drug. In the case in which the estimation target data satisfies the criterion for estimation of taking, the first estimation unit 314 estimates that the subject has taken the drug. On the other hand, in the case in which the estimation target data does not satisfy the criterion for estimation of taking, the first estimation unit 314 estimates that the subject has not taken the drug.

Some examples of the criterion for estimation of taking will be described. The criterion for estimation of taking includes a threshold as described below. The threshold included in the criterion for estimation of taking is also referred to as a first threshold.

In one example of the criterion for estimation of taking, the first threshold is a degree of variation within a predetermined time period starting at a discretionary time. One reason for using this criterion for estimation of taking is that a variation in physical quantity is expected when a subject takes the drug. For example, when the subject uses an antihypertensive agent, a drop in blood pressure is expected. Note that depending on the efficacy of the drug, the variation in the physical quantity may not only be a decrease, but may also be an increase. Note that the length of the predetermined time period can be discretionarily set. The first threshold may be a rate of variation or a variation amount. The first threshold can be discretionarily set.

In this example, the first estimation unit 314 receives biometric data of the subject from the second acquisition unit 313. The first estimation unit 314 acquires the estimation target data from the biometric data of the subject. The first estimation unit 314 finds, on the basis of the estimation target data, a degree of variation of the physical amount within the predetermined time period starting at a discretionary time. The first estimation unit 314 may find the degree of variation of the physical quantity on the basis of the minimum physical quantity and the maximum physical quantity within the predetermined time period. The first estimation unit 314 compares the degree of variation of the physical quantity within the predetermined time period based on the estimation target data to the first threshold included in the criterion for estimation of taking.

In the case in which the degree of variation of the physical quantity is equal to or greater than the first threshold, the first estimation unit 314 estimates that the estimation target data satisfies the criterion for estimation of taking. On the other hand, in the case in which the degree of variation of the physical quantity is less than the first threshold, the first estimation unit 314 estimates that the estimation target data does not satisfy the criterion for estimation of taking. The first estimation unit 314 may, continuously or at certain time intervals, set a discretionary time as the start time. In this way, the first estimation unit 314 can continuously estimate, with varying the starting points, whether or not the subject has taken the drug.

In another example of the criterion for estimation of taking, the first threshold is the degree of divergence from reference data. The reference data is physical quantity data that changes or is assumed to change when the subject has not taken the drug. The reference data is stored in the storage device 34. For example, the reference data is physical quantity data, of the physical quantity data stored in the PHR server 1, of a time period during which the subject did not take the drug. The processor 31 may retrieve the reference data from the PHR server 1 at any time via the communication interface 35 and store the reference data in the storage device 34. The reference data may be data of a typical model, which is assumed to change when the drug is not taken, instead of data based on the physical quantity data of the subject. One reason for using this criterion for estimation of taking is that a divergence to the reference data in physical quantity data is expected when a subject takes the drug. The first threshold may be a rate of divergence or a divergence amount. The first threshold can be discretionarily set.

In this example, the first estimation unit 314 receives biometric data of the subject from the second acquisition unit 313. The first estimation unit 314 acquires the estimation target data from the biometric data of the subject. The first estimation unit 314 compares the physical quantity of the estimation target data to the physical quantity of the reference data included in the criterion for estimation of taking. Note that the first estimation unit 314 preferably compares physical quantities of the same time when comparing the estimation target data and the reference data. For example, the first estimation unit 314 compares the physical quantity of the estimation target data of a certain time to the physical quantity of the reference data of the same time. One reason for this is that the amount of physical quantity and the tendency of variations in the physical quantity are different depending on the time of day. By comparing the physical quantities of the same time, the first estimation unit 314 can improve the estimation accuracy of whether or not the subject has taken the drug.

In the case in which the degree of divergence of the estimation target data to the reference data is equal to or greater than the first threshold, the first estimation unit 314 estimates that the estimation target data satisfies the criterion for estimation of taking. On the other hand, in the case in which the degree of divergence of the estimation target data to the reference data is less than the first threshold, the first estimation unit 314 estimates that the estimation target data does not satisfy the criterion for estimation of taking. Note that in the case in which the degree of divergence of the estimation target data to the reference data is equal to or greater than the first threshold continuously for a certain amount of time, the first estimation unit 314 may estimate that the estimation target data satisfies the criterion for estimation of taking. One reason for this is that even in a situation where the subject is not taking the drug, the physical quantity of the estimation target data may temporarily diverge from the physical quantity of the reference data by the first threshold or greater. By determining whether or not the degree of divergence has continuously been equal to or greater than the first threshold for a certain amount of time, the first estimation unit 314 can improve the estimation accuracy of whether or not the subject has taken the drug. The first estimation unit 314 can continuously estimate whether or not the drug has been taken by continuously comparing the estimation target data with the reference data.

The first estimation unit 314 generates a first estimation result each time it is estimated that the subject has taken one dose of the drug. The first estimation result indicates that the subject took the drug. Furthermore, the first estimation unit 314 includes, in the first estimation result, data indicative of a value based on the estimation target data that has become equal to or greater than the first threshold. In one example, the value based on the estimation target data is the degree of variation of the physical quantity based on the estimation target data. In another example, the value based on the estimation target data is the degree of divergence of the physical quantity based on the estimation target data. The first estimation unit 314 outputs the first estimation result to the second estimation unit 315.

Note that though in the example described above the first estimation unit 314 uses the first threshold to estimate whether or not the subject has taken the drug, the present invention is not limited thereto. The first estimation unit 314 may estimate, on the basis of the physical quantity data without using the first threshold, whether or not the subject has taken the drug.

Note that the first estimation unit 314 identifies the drug prescribed to the subject on the basis of the drug ID data or the drug name data included in the prescription data. The first estimation unit 314 sets the drug prescribed to the subject as a target for estimating whether or not the drug has been taken.

The second estimation unit 315 will be described. As described below, the second estimation unit 315, in response to the first estimation result, estimates, on the basis of the physical quantity data, whether or not the effect of the drug on the subject satisfies the effect estimation criterion. The effect estimation criterion is a standard for estimating whether or not a drug had a predetermined effect on a subject. The effect estimation criterion is predetermined. Some examples of the effect estimation criterion are described below. Note that the second estimation unit 315, in response to acquiring the first estimation result from the first estimation unit 314, estimates whether or not the effect of the drug on the subject satisfies the effect estimation criterion. Thus, the second estimation unit 315 does not estimate whether or not the effect of the drug on the subject satisfies the effect estimation criterion, unless the first estimation unit 314 estimates that the subject has taken the drug.

Some examples of the effect estimation criterion will be described. The effect estimation criterion includes a threshold as described below. The threshold included in the effect estimation criterion is also referred to as a second threshold. The second threshold is greater than the first threshold in absolute value. One reason for this is that the estimation operation by the second estimation unit 315 is premised on the acquisition of the first estimation result. In other words, in the case in which the value based on the estimation target data is equal to or greater than the first threshold, the second estimation unit 315 further evaluates the estimation target data with the second threshold.

In one example of the effect estimation criterion, the second threshold is a degree of variation within a predetermined time period starting at a discretionary time. The second threshold is a degree of variation that is greater than the first threshold. Note that the length of the predetermined time period can be discretionarily set. The second threshold may be a rate of variation or a variation amount. The second threshold can be discretionarily set.

In this example, the second estimation unit 315 receives the first estimation result from the first estimation unit 314. The second estimation unit 315 acquires, from the first estimation result, data indicative of the degree of variation of the physical quantity based on the estimation target data that has become equal to or greater than the first threshold. The second estimation unit 315 compares the degree of variation of the physical quantity based on the estimation target data to the second threshold included in the effect estimation criterion. In the case in which the degree of variation of the physical quantity is equal to or greater than the second threshold, the second estimation unit 315 estimates that the effect of the drug on the subject satisfies the effect estimation criterion. In other words, the second estimation unit 315 estimates that, as a result of the subject taking the drug, the drug has exhibited a predetermined effect on the subject. On the other hand, in the case in which the degree of variation of the physical quantity is less than the second threshold, the second estimation unit 315 estimates that the effect of the drug on the subject does not satisfy the effect estimation criterion. In other words, the second estimation unit 315 estimates that, despite the subject taking the drug, the drug has not exhibited a predetermined effect on the subject. Note that in the case in which the degree of variation of the physical quantity is equal to or greater than the second threshold continuously for a certain amount of time, the second estimation unit 315 may estimate that the estimation target data satisfies the effect estimation criterion. On the other hand, in the case in which the degree of variation of the physical quantity is not equal to or greater than the second threshold continuously for a certain amount of time, the second estimation unit 315 may estimate that the estimation target data does not satisfy the effect estimation criterion.

In another example of the effect estimation criterion, the second threshold is the degree of divergence from reference data. The second threshold is a degree of variation that is greater than the first threshold. The second threshold may be a rate of divergence or a divergence amount. The second threshold can be discretionarily set.

In this example, the second estimation unit 315 receives the first estimation result from the first estimation unit 314. The second estimation unit 315 acquires, from the first estimation result, data indicative of the degree of divergence of the physical quantity based on the estimation target data that has become equal to or greater than the first threshold. The second estimation unit 315 compares the degree of divergence of the physical quantity based on the estimation target data to the second threshold included in the effect estimation criterion. In the case in which the degree of divergence of the physical quantity is equal to or greater than the second threshold, the second estimation unit 315 estimates that the effect of the drug on the subject satisfies the effect estimation criterion. In other words, the second estimation unit 315 estimates that, as a result of the subject taking the drug, the drug has exhibited a predetermined effect on the subject. On the other hand, in the case in which the degree of divergence of the physical quantity is less than the second threshold, the second estimation unit 315 estimates that the effect of the drug on the subject does not satisfy the effect estimation criterion. In other words, the second estimation unit 315 estimates that, despite the subject taking the drug, the drug has not exhibited a predetermined effect on the subject. Note that in the case in which the degree of divergence of the physical quantity is equal to or greater than the second threshold continuously for a certain amount of time, the second estimation unit 315 may estimate that the estimation target data satisfies the effect estimation criterion. On the other hand, in the case in which the degree of divergence of the physical quantity is not equal to or greater than the second threshold continuously for a certain amount of time, the second estimation unit 315 may estimate that the estimation target data does not satisfy the effect estimation criterion.

Note that though in the example described above the second estimation unit 315 uses the second threshold to estimate the effect of the drug, the present invention is not limited thereto. The first estimation unit 314 may estimate, without using the second threshold, whether or not the effect of the drug on the subject satisfies the effect estimation criterion.

The second estimation unit 315 generates a second estimation result each time the effect of the drug on the subject is estimated to not satisfy the effect estimation criterion. The second estimation result indicates that the effect of the drug on the subject does not satisfy the effect estimation criterion. The second estimation unit 315 outputs the second estimation result to the output unit 316.

The output unit 316 will be described. As described below, the output unit 316 outputs, in response to the second estimation result, a support signal supporting a subject. The support signal will be also described later. The output unit 316 receives the second estimation result from the second estimation unit 315. The output unit 316 outputs the support signal in response to acquiring the second estimation result. In other words, in the case in which the effect of the drug on the subject does not satisfy the effect estimation criterion, the output unit 316 outputs the support signal. In the case in which the effect of the drug on the subject satisfies the effect estimation criterion, the output unit 316 does not output a support signal.

The Support signal will be described.

In one example, the support signal is a signal for informing the subject that the effect of the drug on the subject does not satisfy the effect estimation criterion. In this example, the output unit 316 outputs the support signal to the portable terminal of the subject via the communication interface 35. The portable terminal notifies by image or voice, on the basis of the supporting signal, that the effect of the drug on the subject does not satisfy the effect estimation criterion. This allows the subject to contact the hospital and reserve a examination or drug prescription.

In another example, the support signal is a signal for encouraging the subject to reserve a consultation or drug prescription at a hospital. In this example, the output unit 316 outputs the support signal to the EHR server 2 via the communication interface 35. The EHR server 2 executes processing to encourage, on the basis of the support signal, the subject to reserve a consultation or prescription of the drug at a hospital. This allows the subject to contact the hospital and reserve a examination or drug prescription.

3 Operation Example

Drug Management Server

Effect Estimation Operation

FIG. 9 is a flowchart illustrating an example of the effect estimation operation of the drug management server 3.

Note that the processing procedure described below is merely an example, and each process may be changed to the extent possible. Further, in the processing procedure described below, steps can be omitted, substituted, and added as appropriate.

The first acquisition unit 311 acquires the prescription data relating to the drug prescribed to the subject (step S101). In step S101, the first acquisition unit 311 acquires the prescription data of the subject including the drug ID data or the drug name data from the EHR server 2, as described above. The first acquisition unit 311 outputs the prescription data to the determination unit 312, the second acquisition unit 313, and the first estimation unit 314.

The determination unit 312 determines the type of the physical quantity to be acquired (step S102). In step S102, as described above, the determination unit 312 determines, on the basis of the drug ID data or the drug name data included in the prescription data, the type of physical quantity to be acquired. The determination unit 312 outputs a determination result to the second acquisition unit 313.

The second acquisition unit 313 acquires biometric data including the physical quantity data of the subject (step S103). In step S103, the second acquisition unit 313 acquires the biometric data of the subject from the PHR server 1, as described above. The second acquisition unit 313 outputs the biometric data of the subject to the first estimation unit 314.

The first estimation unit 314 estimates whether or not the subject has taken the drug (step S104). In step S104, as described above, the first estimation unit 314 identifies the drug prescribed to the subject on the basis of the prescription data and estimates, on the basis of the physical quantity data, whether or not the subject has taken the drug. The first estimation unit 314 outputs the first estimation result to the second estimation unit 315, in the case in which it is estimated that the subject has taken the drug.

In the case in which it is estimated that the subject has not taken the drug (step S104, No), the first estimation unit 314 repeats the processing of step S104. In the case in which it is estimated that the subject has taken the drug (step S104, Yes), the second estimation unit 315 estimates the effect of the drug (step S105). As described above, in step S105, the second estimation unit 315, estimates, on the basis of the physical quantity data, whether or not the effect of the drug on the subject satisfies the effect estimation criterion. The second estimation unit 315 outputs a second estimation result to the output unit 316 in the case in which the effect of the drug on the subject is estimated to not satisfy the effect estimation criterion.

In the case in which the effect of the drug on the subject is estimated to satisfy the effect estimation criterion (step S105, Yes), the processor 31 ends the effect estimation operation. In the case in which the effect of the drug on the subject is estimated to not satisfy the effect estimation criterion (step S105, No), the output unit 316 outputs the support signal (step S106). In step S106, as described above, the output unit 316 outputs the support signal in response to acquiring the second estimation result.

Note that in step S104, the first estimation unit 314 may specify a time period for estimating, on the basis of the timing of taking drugs and the effect duration, whether or not the subject has taken the drug. The time period specified by the first estimation unit 314 is also referred to as a specified time period. In this example, the first estimation unit 314 receives the prescription data from the first acquisition unit 311. The prescription data includes the timing of taking drugs data and the effect duration data. The first estimation unit 314 acquires the timing of taking drugs data and the effect duration data from the prescription data. The first estimation unit 314 sets the time period for timing of taking drugs indicated in the timing of taking drugs data in accordance with a predetermined rule. The predetermined rule can be discretionarily set. Note that the predetermined rule is preferably a rule in which the time period for timing of taking drugs is set to have a significant length. One reason for this is that an appropriate setting of the time period for timing of taking drugs leads to appropriately specify the time period for estimating whether or not the drug has been taken. The first estimation unit 314 estimates, as a time period for estimating whether or not the drug has been taken, a time period obtained by adding the effect duration indicated in the effect duration data to the time period after conversion. For example, take the example of the timing of taking drugs data being data indicative of the morning and the effect duration data is data indicative of one hour. The first estimation unit 314 sets the time period for timing of taking drugs to be from 6 am to 9 am. The first estimation unit 314 estimates, as a time period for estimating whether or not the drug has been taken, to be from 7 am to 10 am, i.e., the time period of from 6 am to 9 am with one hour added. The first estimation unit 314 estimates, on the basis of the data relating to the specified time period in the physical quantity data, whether or not the drug has been taken. In this way, in the case in which the data relating to the specified time period satisfies the criterion for estimation of taking, the first estimation unit 314 estimates that the subject is taking the drug. On the other hand, in the case in which the data relating to a time period other than the specified time period satisfies the criterion for estimation of taking, the first estimation unit 314 does not estimate that the subject is taking the drug. One reason for this is that even in a situation where the subject is not taking the drug, the value based on the estimation target data may temporarily be equal to or greater than the first threshold. By estimating, on the basis of the data relating the specified time period, whether or not the subject has taken the drug, the first estimation unit 314 can improve the estimation accuracy of whether or not the subject has taken the drug. For example, instances of the first estimation unit 314 incorrectly estimating that the subject has taken the drug even though the subject is not taking the drug can be reduced. Thus, instances of the first estimation unit 314 outputting the first estimation result based on an incorrect estimation to the second estimation unit 315 can be reduced. Since the second estimation unit 315 does not estimate whether or not the effect of the drug on the subject satisfies the effect estimation criterion unless the first estimation result is received, the estimation accuracy can be improved. Note that the first estimation unit 314 may omit the estimation operation in a time period other than the specified time period. Accordingly, the second estimation unit 315 can omit the estimation operation in a time period other than the specified time period.

Note that in step S105, as described below, the second estimation unit 315 may estimate, using a criterion corresponding to a condition of the subject, whether or not the effect of the drug on the subject satisfies the effect estimation criterion. In this example, the second estimation unit 315 receives the prescription data from the first acquisition unit 311. The prescription data includes symptom data. The second estimation unit 315 obtains the symptom data from the prescription data. On the basis of the symptom data, the second estimation unit 315 selects, from among the effect estimation criteria, a criterion corresponding to a symptom of the subject. The effect estimation criteria include a criterion for each symptom. In one example, the criterion for each symptom includes the second threshold of different degrees of variation for each symptom. In another example, the criterion for each symptom includes the second threshold of degree of divergence from different reference data for each symptom. The second estimation unit 315 uses the criterion corresponding to the symptoms of the subject to estimate whether or not the drug has been taken. One reason for the second estimation unit 315 using the criterion corresponding to the symptom of the subject is because the amount of variation of the physical quantity due to taking the drug varies depending on the symptom. For example, with a first symptom, the physical quantity varies greatly depending on taking a first drug, but with a second symptom, variation of the physical quantity may be small depending on taking a second drug. The second estimation unit 315 can improve the estimation accuracy of whether or not the effect of the drug on the subject satisfies the effect estimation criterion, by using a criterion corresponding to the symptom of the subject.

Note that in step S105, as described below, the second estimation unit 315 may estimate, by using a criterion corresponding to the drug prescribed to the subject, whether or not the effect of the drug on the subject satisfies the effect estimation criterion. In this example, the second estimation unit 315 receives the prescription data from the first acquisition unit 311. The prescription data includes at least one of the drug name data or the drug ID data. The second estimation unit 315 acquires at least one of the drug name data or the drug ID data from the prescription data. The second estimation unit 315 selects, on the basis of at least one of the drug name data or the drug ID data, from among the effect estimation criteria, a criterion corresponding to the drug prescribed to the subject. The effect estimation criteria include a criterion for each drug. In one example, the criterion for each drug includes the second threshold of degree of variation that is different for each drug. In another example, the criterion for each drug includes the second threshold of degree of divergence from reference data that is different for each drug. The second estimation unit 315 estimates, by using a criterion corresponding to the drug prescribed to the subject, whether or not the effect of the drug on the subject satisfies the effect estimation criterion. One reason for the second estimation unit 315 using the criterion corresponding to the drug prescribed to the subject is because the amount of variation of the physical quantity varies depending on the drug. For example, with a first symptom, the physical quantity varies greatly depending on taking a first drug, but with a second symptom, variation of the physical quantity may be small depending on taking a second drug. For example, with the same first symptom, the physical quantity varies greatly depending on taking a third drug, but variation of the physical quantity may be small depending on taking a fourth drug. The second estimation unit 315 can improve, by using a criterion corresponding to the drug prescribed to the subject, the estimation accuracy of whether or not the effect of the drug on the subject satisfies the effect estimation criterion.

Note that in step S105, as described below, the second estimation unit 315 may estimate, by using a criterion corresponding to the attributes of the subject whether or not the effect of the drug on the subject satisfies the effect estimation criterion. In this example, the second estimation unit 315 receives the prescription data from the first acquisition unit 311. The second estimation unit 315 receives the biometric data from the second acquisition unit 313. The prescription data or the biometric data includes the attributes data of the subject. The second estimation unit 315 acquires the attributes data of the subject from the prescription data or the biometric data. On the basis of the attributes data of the subject, the second estimation unit 315 selects, from among the effect estimation criteria, a criterion corresponding to an attribute of the subject. The effect estimation criteria include a criterion for each attribute. In one example, the criterion for each attribute includes the second threshold of degree of variation that is different for each attribute. In another example, the criterion for each attribute includes the second threshold of degree of divergence from reference data that is different for each attribute. Note that the effect estimation criterion may include a criterion for each attribute based on any one element (for example, gender). The effect estimation criterion may include a criterion for each attribute based on a combination of any two or more elements (for example, gender and nationality). The second estimation unit 315 uses the criterion corresponding to the attribute of the subject to estimate whether or not the drug has been taken. One reason for the second estimation unit 315 using the criterion corresponding to the attribute of the subject is because the amount of variation of the physical quantity due to taking the drug varies depending on the attribute. For example, with a first attribute, the physical quantity varies greatly depending on taking the drug, but with a second attribute, variation of the physical quantity may be small depending on taking the same drug. The second estimation unit 315 can improve, by using a criterion corresponding to the attribute of the subject, the estimation accuracy of whether or not the subject has taken the drug.

4 Action and Effect

As described above, in the present embodiment, the drug management server 3 is capable of estimating, on the basis of the physical quantity data, whether or not the effects of the drug on the subject satisfy the effect estimation criterion, in response to the estimation result indicating that the subject used the drug.

The drug management server 3 can improve the estimation accuracy of the effect of the drug on the subject by assuming an estimated operation of taking the drug as a premise of an estimated operation of the effect of the drug.

Furthermore, in the present embodiment, the drug management server 3 can determine, on the basis of the drug ID data or the drug name data, the type of physical quantity to be acquired.

The physical quantity that varies is different depending on the drug. The drug management server 3 can determine, on the basis of the drug ID data or the drug name data, the type of physical quantity data suitable for estimating whether or not the subject has taken the drug and for estimating the effect of the drug on the subject.

Furthermore, in the present embodiment, the drug management server 3 can output, in response to the second estimation result, a support signal supporting the subject, indicating that the effect of the drug does not satisfy the effect estimation criterion.

This allows the drug management server 3 to notify the subject that the effect of the drug does not satisfy the effect estimation criterion and encourage the subject to reserve a consultation or prescription of the drug at a hospital. The drug management server 3 can use the effect estimation criterion for each person to perform support on each person without variation.

Furthermore, in the present embodiment, the drug management server 3 can estimate, on the basis of data relating to a specified time period in the physical quantity data, whether or not the subject has taken the drug.

Even in a situation where the subject is not taking the drug, the value based on the estimation target data may temporarily be equal to or greater than the first threshold. By estimating, on the basis of the data relating to the specified time period, whether or not the subject has taken the drug, the drug management server 3 can improve the estimation accuracy of whether or not the subject has taken the drug. As a result, the drug management server 3 can improve the estimation accuracy of whether or not the effect of the drug on the subject satisfies the effect estimation criterion. Furthermore, the drug management server 3 can reduce the load of the estimation operation by omitting the estimation operation in time periods other than the specified time period.

Furthermore, in the present embodiment, the drug management server 3 can estimate, by using a criterion corresponding to a symptom of the subject included in the effect estimation criterion, whether or not the effect of the drug on the subject satisfies the effect estimation criterion.

The amount of variation of the physical quantity due to taking the drug is different depending on the symptom. The drug management server 3 can improve, by using the criterion corresponding to the symptom of the subject, the estimation accuracy of the effect of the drug on the subject.

Furthermore, in the present embodiment, the drug management server 3 can estimate, by using a criterion corresponding to the drug prescribed to the subject included in the effect estimation criterion, whether or not the effect of the drug on the subject satisfies the effect estimation criterion.

Even with the same symptom, the amount of variation of the physical quantity is different depending on the drug taken by the subject. The drug management server 3 can improve, by using the criterion corresponding to the drug prescribed to the subject, the estimation accuracy of the effect of the drug on the subject.

Furthermore, in the present embodiment, the drug management server 3 can estimate, by using a criterion corresponding to an attribute of the subject included in the effect estimation criterion, whether or not the effect of the drug on the subject satisfies the effect estimation criterion.

When people with different attributes take the same drug, the amount of variation of the physical quantity is different. The drug management server 3 can improve, by using the criterion corresponding to the attribute of the subject, the estimation accuracy of the effect of the drug on the subject.

5 Modified Examples

5-2 Modified Example 1

In the present embodiment, the drug management server 3 is configured of different hardware to the PHR server 1 and the EHR server 2, but no such limitation is intended. The drug management server 3 may be formed integrally with the PHR server 1. The drug management server 3 may be formed integrally with the EHR server 2. Also, the above-described residual drug amount estimation operation may be performed, not limited to the drug management server 3, by various devices such as a portable terminal or a measurement instrument that measures a physical quantity of the living body.

5-2 Modified Example 2

In short, the invention is not limited to the present embodiment and can be embodied by modifying the components in an implementation stage in a range without departing from the gist thereof. Further, various inventions can be formed by appropriately combining a plurality of constituent elements disclosed in the present embodiment. For example, some constituent elements may be omitted from the entire constituent elements shown in the embodiment. Furthermore, the constituent elements of different embodiments may be combined appropriately.

6 Supplementary Notes

A part or all of the present embodiment may also be described as supplementary notes below in addition to claims, which is not limited thereto.

Supplementary Note

A drug management device (3) includes a first acquisition unit (311) configured to acquire prescription data including data indicative of a drug prescribed to a subject, a second acquisition unit (313) configured to acquire biometric data including data indicative of variations in a physical quantity of a living body of the subject, a first estimation unit (314) configured to estimate, on the basis of the data indicative of variations in the physical quantity, whether or not the subject has taken the drug, and a second estimation unit (315) configured to, in response to an estimation result indicating that the subject has taken the drug, estimate, on the basis of the data indicative of variations in the physical quantity, whether or not an effect of the drug on the subject satisfies an effect estimation criterion, the effect estimation criterion being predetermined.

REFERENCE SIGNS LIST

1 PHR server
2 EHR server
3 Drug management server
11 Processor
12 ROM
13 RAM
14 Storage device
15 Communication interface
21 Processor
22 ROM
23 RAM
24 Storage device
25 Communication interface
31 Processor
32 ROM
33 RAM
34 Storage device
35 Communication interface
100 Drug management system
311 First acquisition unit
312 Determination unit
313 Second acquisition unit
314 First estimation unit
315 Second estimation unit
316 Output unit

The invention claimed is:

1. A drug management device, comprising:
one or more processors configured to:
acquire prescription data including data indicative of a drug prescribed to a subject, data indicative of timing of taking the drug, and data indicative of effect duration after taking the drug;
determine a type of a physical quantity of a living body to be acquired that is assumed to vary due to a drug specified by the data indicative of the drug prescribed to the subject, by referencing a database in which a drug and a physical quantity of a living body assumed to vary due to the drug are associated;
acquire biometric data including data indicative of variations in a physical quantity of the living body of the subject to be acquired;
set a time period of the timing of taking in accordance with a predetermined rule, specify a time period, obtained by adding the effect duration to each of two times of the time period of the timing of taking, as a specified time period for estimating whether or not the drug has been taken, and estimate, on the basis of data relating to the specified time period among the data indicative of variations in the physical quantity, whether or not the subject has taken the drug; and
in response to an estimation result indicating that the subject has taken the drug, estimate, on the basis of the data indicative of variations in the physical quantity, whether or not an effect of the drug on the subject satisfies an effect estimation criterion, the effect estimation criterion being predetermined.

2. The drug management device according to claim 1, further comprising an output configured to output a signal for supporting the subject in response to an estimation result indicating that an effect of the drug on the subject does not satisfy the effect estimation criterion.

3. The drug management device according to claim 1, wherein
the prescription data includes data indicative of a symptom of the subject,
the effect estimation criterion includes a criterion for each symptom, and
the one or more processors estimates, with using a criterion corresponding to a symptom of the subject, whether or not an effect of the drug on the subject satisfies the effect estimation criterion.

4. The drug management device according to claim 1, wherein
the effect estimation criterion includes a criterion for each drug, and
the one or more processors estimates, with using a criterion corresponding to the drug prescribed to the subject, whether or not an effect of the drug on the subject satisfies the effect estimation criterion.

5. The drug management device according to claim 1, wherein
the prescription data or the biometric data includes data indicative of an attribute of the subject,
the effect estimation criterion includes a criterion for each attribute, and
the one or more processors estimates, with using a criterion corresponding to an attribute of the subject, whether or not an effect of the drug on the subject satisfies the effect estimation criterion.

6. A drug management method, comprising:
a first acquisition step of acquiring prescription data including data indicative of a drug prescribed to a subject, data indicative of timing of taking the drug, and data indicative of effect duration after taking the drug;
a determination step of determining a type of a physical quantity of a living body to be acquired that is assumed to vary due to a drug specified by the data indicative of the drug prescribed to the subject, by referencing a database in which a drug and a physical quantity of a living body assumed to vary due to the drug are associated;
a second acquisition step of acquiring biometric data including data indicative of variations in physical quantity, of the living body of the subject to be acquired;
a first estimation step of setting a time period of the timing of taking in accordance with a predetermined rule, specifying a time period, obtained by adding the effect duration to each of two times of the time period of the timing of taking, as a specified time period for estimating whether or not the drug has been taken, and estimating, on the basis of data relating to the specified time period among the data indicative of variations in the physical quantity, whether or not the subject has taken the drug; and
a second estimation step of, in response to an estimation result indicating that the subject has taken the drug, estimating, on the basis of the data indicative of variations in the physical quantity, whether or not an effect of the drug on the subject satisfies an effect estimation criterion, the effect estimation criterion being predetermined.

7. A non-transitory recording medium storing a program, executable by one or more processors, for drug management to perform a drug management method, comprising:
a first acquisition step of acquiring prescription data including data indicative of a drug prescribed to a subject, data indicative of timing of taking the drug, and data indicative of effect duration after taking the drug;
a determination step of determining a type of a physical quantity of a living body to be acquired that is assumed to vary due to a drug specified by the data indicative of the drug prescribed to the subject, by referencing a database in which a drug and a physical quantity of a living body assumed to vary due to the drug are associated;
a second acquisition step of acquiring biometric data including data indicative of variations in physical quantity, of the living body of the subject to be acquired;
a first estimation step of setting a time period of the timing of taking in accordance with a predetermined rule, specifying a time period, obtained by adding the effect duration to each of two times of the time period of the timing of taking, as a specified time period for estimating whether or not the drug has been taken, and estimating, on the basis of data relating to the specified time period among the data indicative of variations in the physical quantity, whether or not the subject has taken the drug; and
a second estimation step of, in response to an estimation result indicating that the subject has taken the drug, estimating, on the basis of the data indicative of variations in the physical quantity, whether or not an effect of the drug on the subject satisfies an effect estimation criterion, the effect estimation criterion being predetermined.

* * * * *